(12) United States Patent
Fang et al.

(10) Patent No.: US 10,510,623 B2
(45) Date of Patent: Dec. 17, 2019

(54) OVERLAY ERROR AND PROCESS WINDOW METROLOGY

(71) Applicant: Taiwan Semiconductor Manufacturing Co., Ltd., Hsinchu (TW)

(72) Inventors: Shang-Wei Fang, Hsinchu County (TW); Jing-Sen Wang, Hsinchu (TW); Yuan-Yao Chang, Kaohsiung (TW); Wei-Ray Lin, Hsinchu (TW); Ting-Hua Hsieh, Hsinchu (TW); Pei-Hsuan Lee, Taipei (TW); Yu-Hsuan Huang, Taichung (TW)

(73) Assignee: TAIWAN SEMICONDUCTOR MANUFACTURING CO., LTD., Hsinchu (TW)

( * ) Notice: Subject to any disclaimer, the term of this patent is extended or adjusted under 35 U.S.C. 154(b) by 0 days.

(21) Appl. No.: 15/855,080

(22) Filed: Dec. 27, 2017

(65) Prior Publication Data
US 2019/0198403 A1  Jun. 27, 2019

(51) Int. Cl.
| | |
|---|---|
| *H01L 21/66* | (2006.01) |
| *G03F 7/20* | (2006.01) |
| *G06F 17/50* | (2006.01) |
| *H01L 21/768* | (2006.01) |
| *G01N 21/88* | (2006.01) |
| *H01L 21/76* | (2006.01) |
| *G01N 21/95* | (2006.01) |
| *G01N 21/93* | (2006.01) |
| *G06T 7/00* | (2017.01) |
| *H01L 21/8234* | (2006.01) |

(52) U.S. Cl.
CPC ......... *H01L 22/12* (2013.01); *G01N 21/8851* (2013.01); *G01N 21/93* (2013.01); *G01N 21/9501* (2013.01); *G06T 7/001* (2013.01); *G01N 2021/8883* (2013.01); *G06T 2207/30148* (2013.01); *H01L 21/823418* (2013.01); *H01L 21/823431* (2013.01); *H01L 21/823437* (2013.01); *H01L 21/823475* (2013.01)

(58) Field of Classification Search
CPC ............. G06F 17/5068; G06F 17/5081; G06F 2217/12; G06F 2217/06; Y02P 90/265
See application file for complete search history.

(56) References Cited

U.S. PATENT DOCUMENTS

| | | | |
|---|---|---|---|
| 6,251,745 B1 * | 6/2001 | Yu ........................ | G03F 7/70633 257/E21.53 |
| 7,439,084 B2 | 10/2008 | Hiang et al. | |
| | (Continued) | | |

*Primary Examiner* — Brian Turner
(74) *Attorney, Agent, or Firm* — McClure, Qualey & Rodack, LLP

(57) ABSTRACT

A method for inline inspection during semiconductor wafer fabrication is provided. The method includes forming a plurality of test structures on a semiconductor wafer along two opposite directions. An offset distance between a sample feature and a target feature of each of the test structures increases gradually along the two opposite directions. The method further includes producing an image of the test structures. The method also includes performing image analysis of the image to recognize a position with an extreme of a gray level. In addition, the method includes calculating an overlay error according to the recognized position.

20 Claims, 16 Drawing Sheets

(56) References Cited

U.S. PATENT DOCUMENTS

| | | | | |
|---|---|---|---|---|
| 2004/0188643 A1* | 9/2004 | Weiss | ............... | G01N 21/21 |
| | | | | 250/559.42 |
| 2004/0191652 A1* | 9/2004 | Dishon | ............... | G03F 7/3028 |
| | | | | 430/30 |
| 2007/0184628 A1* | 8/2007 | Yang | ............... | G03F 7/70633 |
| | | | | 438/401 |
| 2010/0030360 A1* | 2/2010 | Habets | ............... | G03F 7/705 |
| | | | | 700/110 |
| 2014/0375793 A1* | 12/2014 | Harada | ............... | H01L 23/544 |
| | | | | 348/80 |
| 2015/0067617 A1* | 3/2015 | Chang | ............... | G06F 17/5081 |
| | | | | 716/52 |
| 2016/0155662 A1* | 6/2016 | Lee | ............... | H01L 21/0337 |
| | | | | 438/668 |
| 2017/0138725 A1* | 5/2017 | Kawada | ............... | G01B 15/00 |
| 2017/0322021 A1* | 11/2017 | Takagi | ............... | G01B 15/04 |

* cited by examiner

OVERLAY ERROR AND PROCESS WINDOW METROLOGY

BACKGROUND

The semiconductor integrated circuit (IC) industry has experienced exponential growth. Technological advances in IC materials and design have produced generations of ICs where each generation has smaller and more complex circuits than the previous generation. In the course of IC evolution, functional density (i.e., the number of interconnected devices per chip area) has generally increased while geometric size (i.e., the smallest component (or line) that can be created using a fabrication process) has decreased. This scaling-down process generally provides benefits by increasing production efficiency and lowering associated costs. Such scaling-down has also increased the complexity of processing and manufacturing ICs.

IC design becomes more challenging as IC technologies continually progress towards smaller features. For example, an IC device includes a sequence of patterned layers and un-patterned layers that combine to form one or more IC features. Misalignment between the various layers can cause performance issues and even potentially cause an IC device to fail due to, for example, a short caused by misaligned layers. Overlay (generally referring to layer-to-layer positioning) of the various layers is thus a factor to ensuring the IC device and/or IC features function properly, and in particular, function according to design requirements for the IC device and/or IC feature.

In addition, a process window refers to the range of focus and exposure settings that will still produce the desired features into the photo-resist layer. For example, the smaller process window results in design rules requiring a minimum spacing between the contact openings and device features (e.g., gate structures), which provides a smaller than desirable margin of contact/gate structure overlay. Further, if the minimum spacing between the contact openings and such device features varies, poor device performance results, such as contact/gate structure short and contact open issue.

Although existing overlay error metrology techniques and process window improvement method have been generally adequate for their intended purposes, they have not been entirely satisfactory in when it comes to quickly and accurately assessing overlay issues for advanced technology nodes.

BRIEF DESCRIPTION OF THE DRAWINGS

Aspects of the present disclosure are best understood from the following detailed description when read with the accompanying figures. It should be noted that, in accordance with the standard practice in the industry, various features are not drawn to scale. In fact, the dimensions of the various features may be arbitrarily increased or reduced for clarity of discussion.

DETAILED DESCRIPTION

Figure 1:
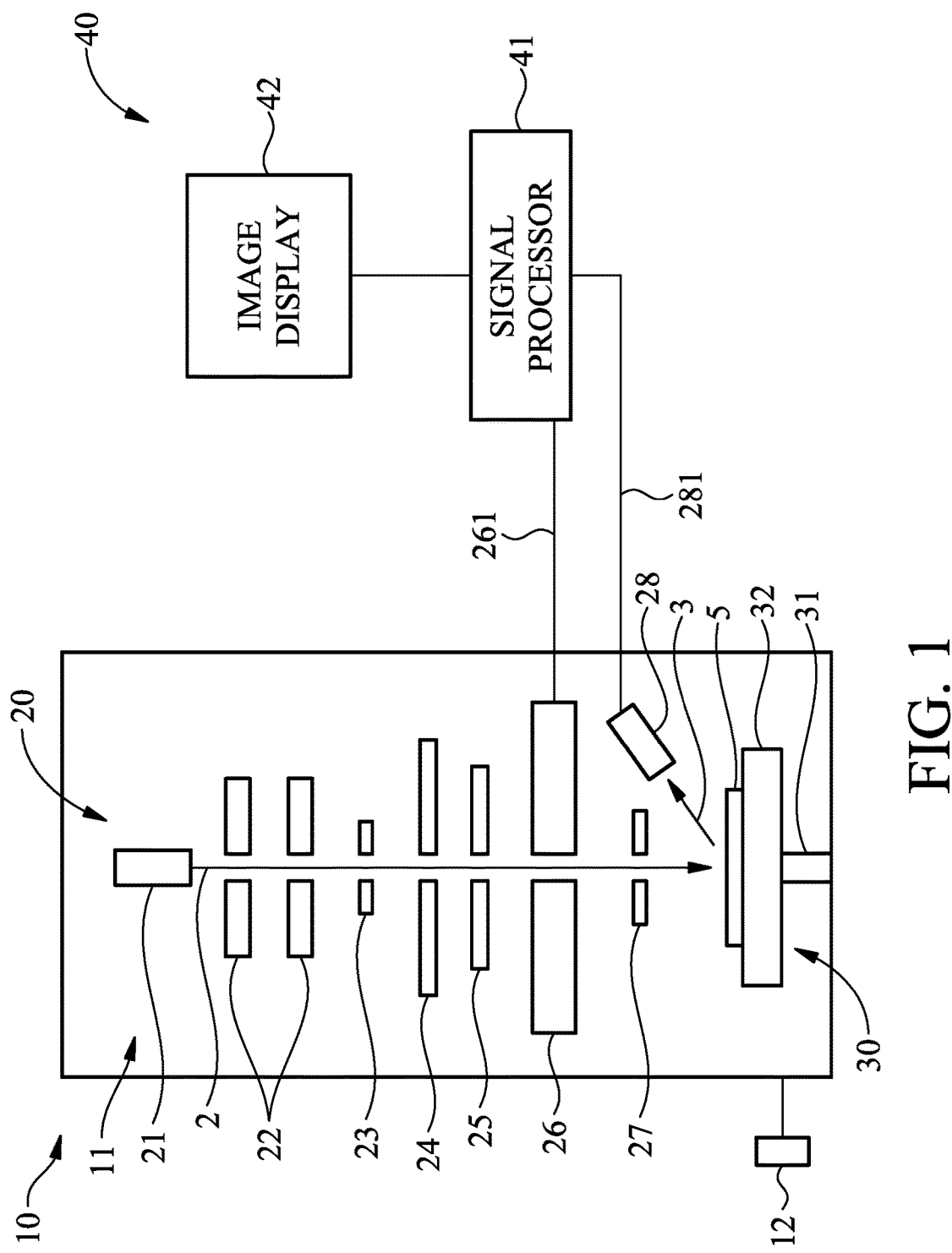
FIG. 1 is a cross-sectional view of a wafer inspecting apparatus for inspecting a semiconductor wafer in a semiconductor manufacturing process, in accordance with some embodiments.

The following disclosure provides many different embodiments, or examples, for implementing different features of the subject matter provided. Specific examples of solutions and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Furthermore, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly. It should be understood that additional operations can be provided before, during, and after the method, and some of the operations described can be replaced or eliminated for other embodiments of the method.

The advanced lithography process, method, and materials described in the current disclosure can be used in many applications, including fin-type field effect transistors (FinFETs). For example, the fins may be patterned to produce a relatively close spacing between features, for which the above disclosure is well suited. In addition, spacers used in forming fins of FinFETs can be processed according to the above disclosure.

FIG. 1 is a cross-sectional view of a wafer inspecting apparatus 1 for inspecting a semiconductor wafer 5 in the semiconductor manufacturing process, in accordance with some embodiments. In some embodiments, the wafer inspecting apparatus 1 includes a chamber assembly 10, an image capturing assembly 20, a wafer stage assembly 30, and an image processing assembly 40. In some embodiments, the wafer inspecting apparatus 1 is configured to produce magnify images of the semiconductor wafer 5. The elements of the wafer inspecting apparatus 1 can be added to or omitted, and the disclosure should not be limited by the embodiments.

The chamber assembly 10 has an enclosure 11 for receiving the semiconductor wafer 5 for performing the wafer inspection process. The image capturing assembly 20 and the wafer stage assembly 30 are positioned in the chamber assembly 10. In some embodiments, the chamber assembly 10 includes a vacuum producer 12. The vacuum producer 12 is configured to produce a vacuum in the enclosure 11. The vacuum producer 12 includes, for example, a fan, a blower, or a pump. In some embodiments, the enclosure 11 is kept in a high vacuum, for example, enclosure 11 is operating at about $10^{-6}$ Torr. Therefore, the scattering of the charged particle beam from the image capturing assembly 20 before reaching the semiconductor wafer 5 is minimized.

The image capturing assembly 20 is configured to produce and direct a charged particle beam 2 into the semiconductor wafer 5. In some embodiments, the image capturing assembly 20 includes a charged particle source 21 configured to emit a charged particle beam. In some embodiments, the charged particle source 21 is an electron gun fitted with a tungsten filament cathode. A charged particle beam is emitted from an electron gun. The electron gun may be made of a metal such as tungsten which has the highest melting point and lowest vapor pressure of all metals. As a result, the electron gun allows it to be heated for electron emission. In some embodiments, the charged particle beam from the charged particle source 21 has an energy ranging from about 100 eV to about 3000 eV.

In some embodiments, the image capturing assembly 20 further includes a number of elements arranged in a column to direct a charged particle beam from the charged particle source 21 to the semiconductor wafer 5. For example, the image capturing assembly 20 further includes a cap 22, an accelerating electrode 23, an upper stage condenser 24, a lower stage condenser 25, a objective lens 26, a scan coil 27, and a detector 28. It is appreciated that the elements of the image capturing assembly 20 can be added to or omitted, and the disclosure should not be limited by the embodiments.

In some embodiments, the cap 22 is configured to shape the charged particle beam. The cap 22 may surround the charged particle source 21 and has a small hole in the center through which electrons exit.

In some embodiments, the accelerating electrode 23 is configured to supply an acceleration voltage to the charged particle beam 2. The accelerating electrode 23 is positioned below the cap 22 to attract the charged particle beam 2 away from the charged particle source 21. Typically, an increase in acceleration voltage will result in most charged particle beams 2 (i.e., primary electrons) traveling deeper within the semiconductor wafer 5. Therefore, a higher signal (and lower noise) in the final image is received by the detector 28.

The upper stage condenser 24, the lower stage condenser 25, and the objective lens 26 are configured to reduce the diameter of the charged particle beam 2. In some embodiments, each of the upper stage condenser 24, the lower stage condenser 25, and the objective lens 26 is an electromagnetic lens including a coil of wire through which electrical current flows.

In some embodiments, the upper stage condenser 24 and the lower stage condenser 25 are configured to reduce the diameter of the source of electrons and to place a small, focused beam of electrons (or a spot) onto the semiconductor wafer 5. In some embodiments, the upper stage condenser 24 and the lower stage condenser 25 converge the cone of the charged particle beam to a spot below it, before the cone flares out again and is converged back again by the objective lens and down onto the semiconductor wafer 5. Since the upper stage condenser 24 and the lower stage condenser 25 control the initial spot size of the charged particle beam, the upper stage condenser 24 and the lower stage condenser 25 are collectively referred to as the spot size controller. The diameter of this initial convergence (also called the cross-over point) affects the final diameter of the spot that the beam makes on the sample.

In some embodiments, the objective lens 26 is configured to focus the charged particle beam 2 into a spot on the semiconductor wafer 5. The strength of the electrical current applied to the objective lens changes the position of the point at which the charged particle beam is focused on the semiconductor wafer. The charged particle beam can be focused at different working distances (the distance between the lower objective lens and the point of focus on the semiconductor wafer).

For example, the charged particle beam can be focused below the process surface of the semiconductor wafer 5. Alternatively, the charged particle beam can be focused above the process surface of the semiconductor wafer 5. Alternatively, the charged particle beam can be focused just right at the process surface of the semiconductor wafer 5. The objective lens 26 may be in signal communication e.g., electrical signal line 261 with the image processing assembly 40.

In some embodiments, the scan coil 27 is configured to deflect the charged particle beam 2 in the X and Y axes so that it scans in a raster fashion over a test region (not shown in FIG. 1) of the process surface of the semiconductor wafer 5. The scan coil 27 may include a number of conductive plates. Sets of the plates are arranged around the path along which the charged particle beam passes. By varying the potential between them, the charged particle beam can be deflected.

In some embodiments, the detector 28 is configured to detect radiation beams produced from the semiconductor wafer 5. For example, the detector 28 is used to receive a secondary electron 3 which is expelled from the semiconductor wafer 5 after the incident of the charged particle beam 2 into the semiconductor wafer 5.

In some embodiments, the detector 28 is positioned at a predetermined angle above and to one side of the wafer stage assembly 30 to capture the secondary electrons 3 emitted from the sample surface following the primary charged particle beam 2 impacts. The detector 28 may be supplied with about a 10 keV positive potential on its face, so as to attract the secondary electrons 3 emitted from the process surface of the semiconductor wafer 5. The detector 28 may be in signal communication e.g., electrical signal line 281 with the image processing assembly 40.

The image processing assembly 40 includes a signal processor 41 and an image display 42. In some embodiments, the signal processor 41 includes a signal processing unit for processing the signal prior to the transfer to the image display 42 to produce a brightness contrast image representative of an electrical resistance in conductive portions of the IC to aid in electrical failure analysis of conductive portions, e.g., conductive interconnect wiring of the IC sample.

The image display 42 displays an image of a portion of the sample in response to the input signal to the signal processor 41 and the output signal to the image display 42. The input signal to the signal processor 41, for example a current signal from the detector 28, is processed by the signal processor 41 with the aid of information supplied by the objective lens 26. Therefore, a displayed image corresponding to an area scanned by the primary charged particle beam is shown in the image display 42.

In some embodiments, the image processing assembly 40 is supplied with automated controls for adjusting the various beam parameters. In some embodiments, the image processing assembly 40 is provided with a computer controlled graphical user interface including displays of the various beam parameters including electron beam voltage. In some embodiments, the image processing assembly 40 is equipped with a processing system for retrieving and storing electron beam condition parameters.

The wafer stage assembly 30 is configured for holding, positioning, moving, and otherwise manipulating the semiconductor wafer 5. In some embodiments, the wafer stage assembly 30 includes an actuator 31 and a wafer holder 32. The actuator 31, for example, a step motor, is coupled to the wafer holder 32 to drive the wafer holder 32. As a result, the wafer holder 32 is designed and configured to be operable for translational and rotational motions.

In some embodiments, the wafer holder 32 is further designed to tilt or dynamically change the tilt angle. In some embodiments, a desired working distance between the objective lens 26 and the process surface (i.e., top surface) of the semiconductor wafer 5 is controlled by the actuator 31. The semiconductor wafer 5 may be secured on the wafer holder 32 by a clamping mechanism, such as vacuum clamping or e-chuck clamping. In some embodiments, the wafer holder 32 is fitted with a suitable mechanism to provide electrical current to the semiconductor wafer 5 so as to improve inspecting resolution.

In some embodiments, the semiconductor wafer 5 is electrically grounded via the wafer holder 32. In some embodiments, the wafer holder 32 is positively charged. Negatively charged electrons are attracted to the positively charged semiconductor wafer 5 and move toward it. Electrons that are not absorbed by the semiconductor wafer 5 may travel to the positively charged wafer holder 32.

Figure 2:
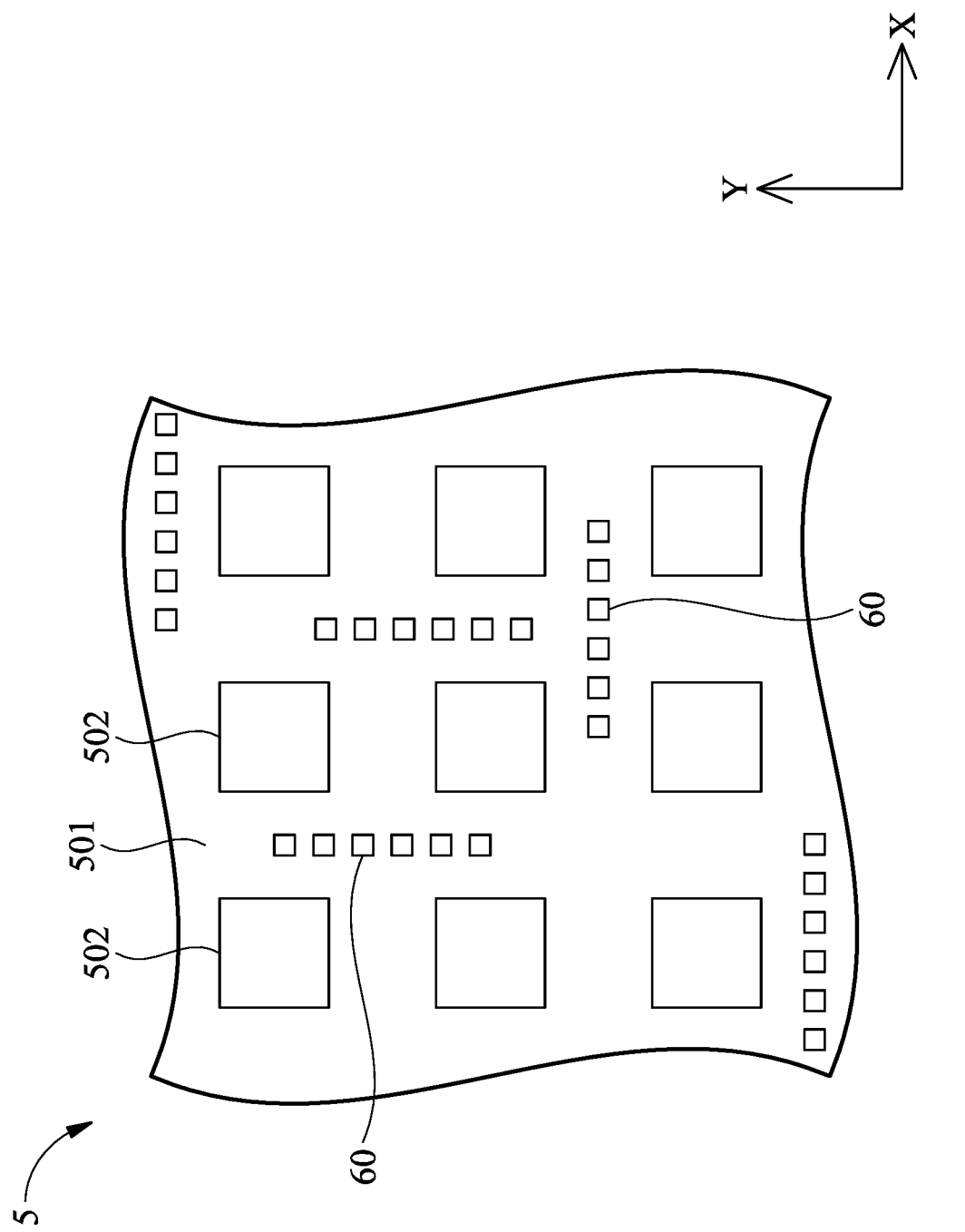
FIG. 2 is a plan view of a portion of a semiconductor wafer, in accordance with some embodiments.

FIG. 2 shows a plan view of a portion of the semiconductor wafer 5, in accordance with some embodiments. A number of dies 502 are formed on a semiconductor wafer 5 by performing semiconductor processing including lithography, etch, ion implant and thin film processes. The wafer spaces between the IC die are referred to as scribe line 501. The scribe lines 501 are used for sawing the semiconductor wafer 5 after the process of the metal layers M1-M5 (FIG. 4) are finished. In some embodiments, a number of test keys 60 are formed in the scribe lines 501 between adjacent dies 502. Some of the test keys 60 extend in a longitudinal direction (i.e. the X-axis), and some of test keys 60 extend in a traversal direction (i.e. the Y-axis). Additional details of the structural features of the test keys 60, in accordance with some embodiments, are described below with respect to FIGS. 4-8.

Figure 3:
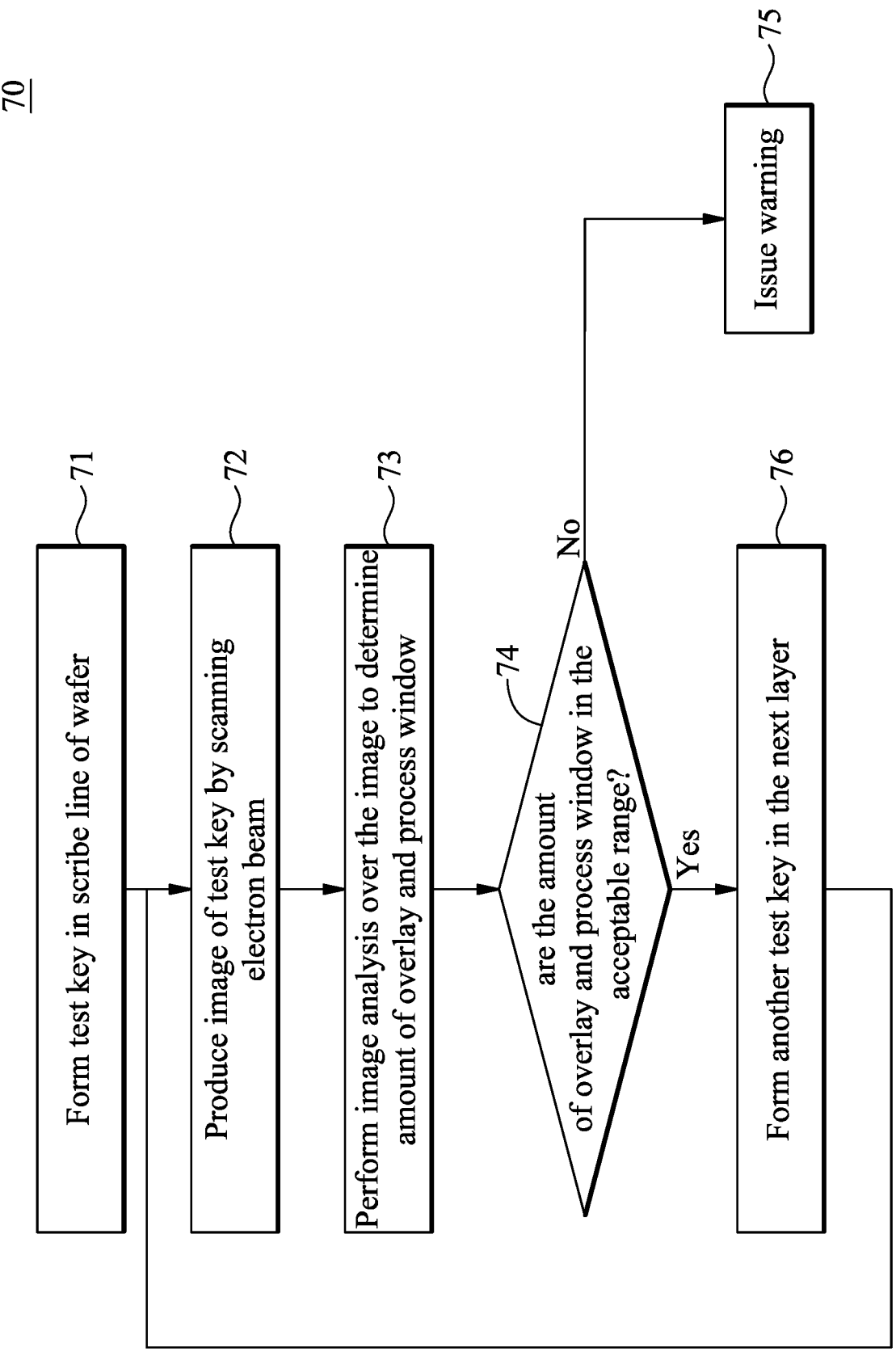
FIG. 3 is a flow chart illustrating a method for performing an in-line monitoring process over a semiconductor wafer, in accordance with some embodiments.

FIG. 3 is a flow chart illustrating a method 70 for performing the in-line (during the manufacturing process) monitoring process on the semiconductor wafer 5, in accordance with some embodiments. For illustration, the flow chart will be described in company with the schematic views shown in FIGS. 1-2 and 4-9. Some of the stages described can be replaced or eliminated for different embodiments.

Figure 4:
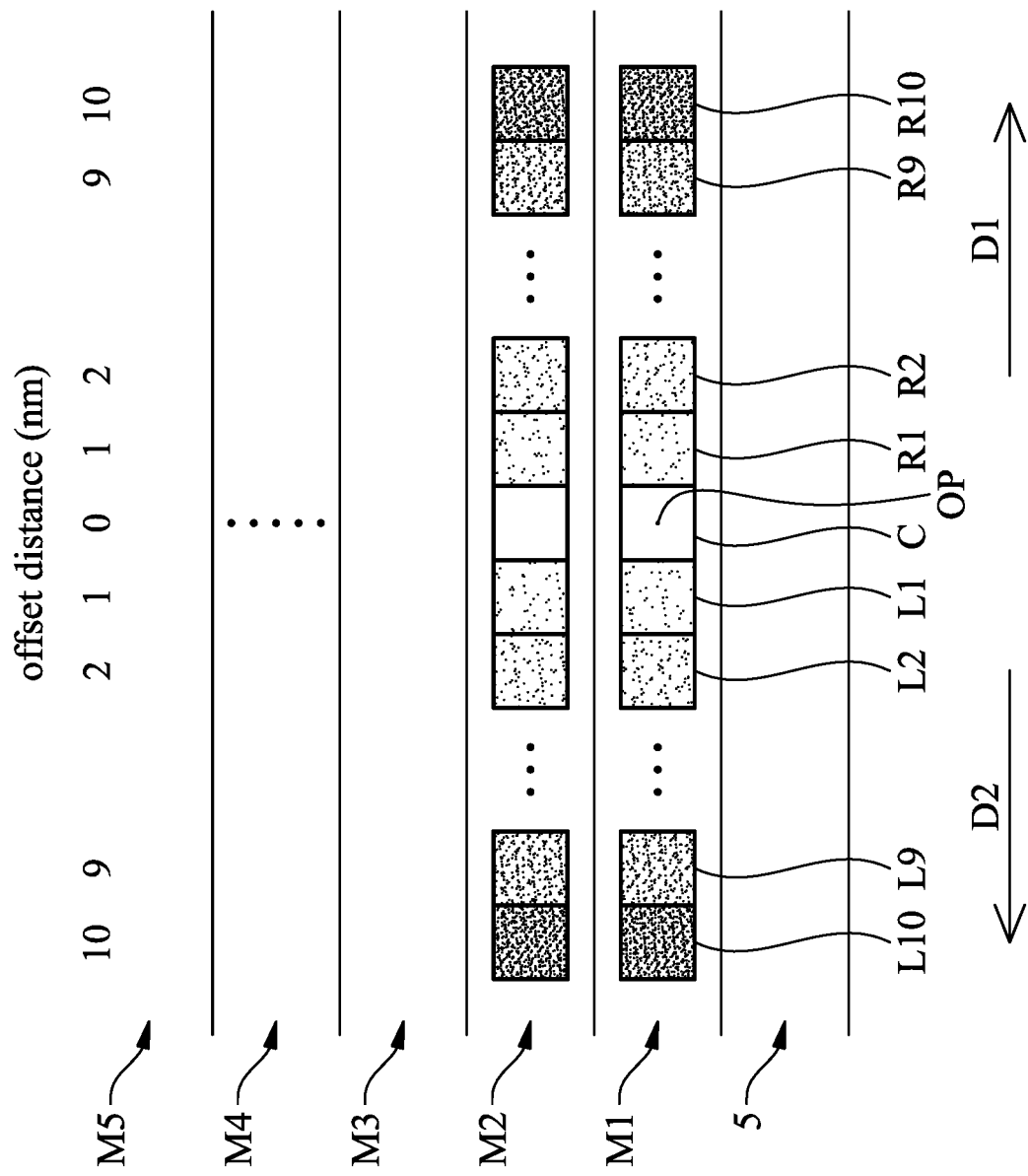
FIG. 4 is a diagram of a number of test keys formed in different stacked layers, wherein a VC image of test structure of the test keys shows different gray levels, in accordance with some embodiments.

The method 70 includes operation 71, in which a layer including a number of test keys 60 is formed on the semiconductor wafer 5. In some embodiments, as shown in FIG. 4, a layer M1 is stacked on the semiconductor wafer 5. The layer M1 includes a number of electronic devices, such as resistors, capacitors, inductors, diodes, transistors, or the like in the wafer die 502. In addition, the layer M1 also includes one or more test keys 60 formed in the scribe lines 501.

In some embodiments, the test key 60 in the first layer M1 includes a number of test structures, such as the central test structure C, the first group of test structures R1, R2 . . . R9 and R10, and the second group of test structures L1, L2 . . . L9 and L10. The central test structure C is positioned in an original position OP.

The first group of test structures R1, R2 . . . R9 and R10 are arranged in order along the first direction D1 from the original position OP. Specifically, the test structure R1 is positioned at a side of the central test structure C in the first direction D1. The test structure R2 is positioned at a side of the test structure R1 in the first direction D1. The test structure R9 is positioned at a side of the test structure R2 in the first direction D1. Another six test structures (not shown in figures) are positioned between the test structure R2 and the test structure R9. The test structure R10 is positioned at a side of the test structure R9 in the first direction D1.

In some embodiments, two neighboring test structures of the first group of test structures R1, R2 . . . R9 and R10 are directly connected to each other. However, it should be appreciated that many variations and modifications can be made to embodiments of the disclosure. In some other embodiments, two neighboring test structures of the first group of test structures R1, R2 . . . R9 and R10 are distant away from each other by a predetermined width.

The second group of test structures L1, L2 . . . L9 and L10 are arranged in order along the second direction D2 from the original position OP. The second direction D2 is opposite to the first direction D1. Specifically, the test structure L1 is positioned at the side of the central test structure C in the second direction D2. The test structure L2 is positioned at a side of the test structure L1 in the second direction D2. The test structure L9 is positioned at a side of the test structure L2 in the second direction D2. Another six test structures (not shown in figures) are positioned between the test structure L2 and the test structure L9. The test structure L10 is positioned at a side of the test structure L9 in the second direction D2.

In some embodiments, two neighboring test structures of the second group of test structures L1, L2 . . . L9 and L10 are directly connected to each other. However, it should be appreciated that many variations and modifications can be made to embodiments of the disclosure. In some other embodiments, two neighboring test structures of the second group of test structures L1, L2 . . . L9 and L10 are distant away from each other by a predetermined width.

Figure 5:
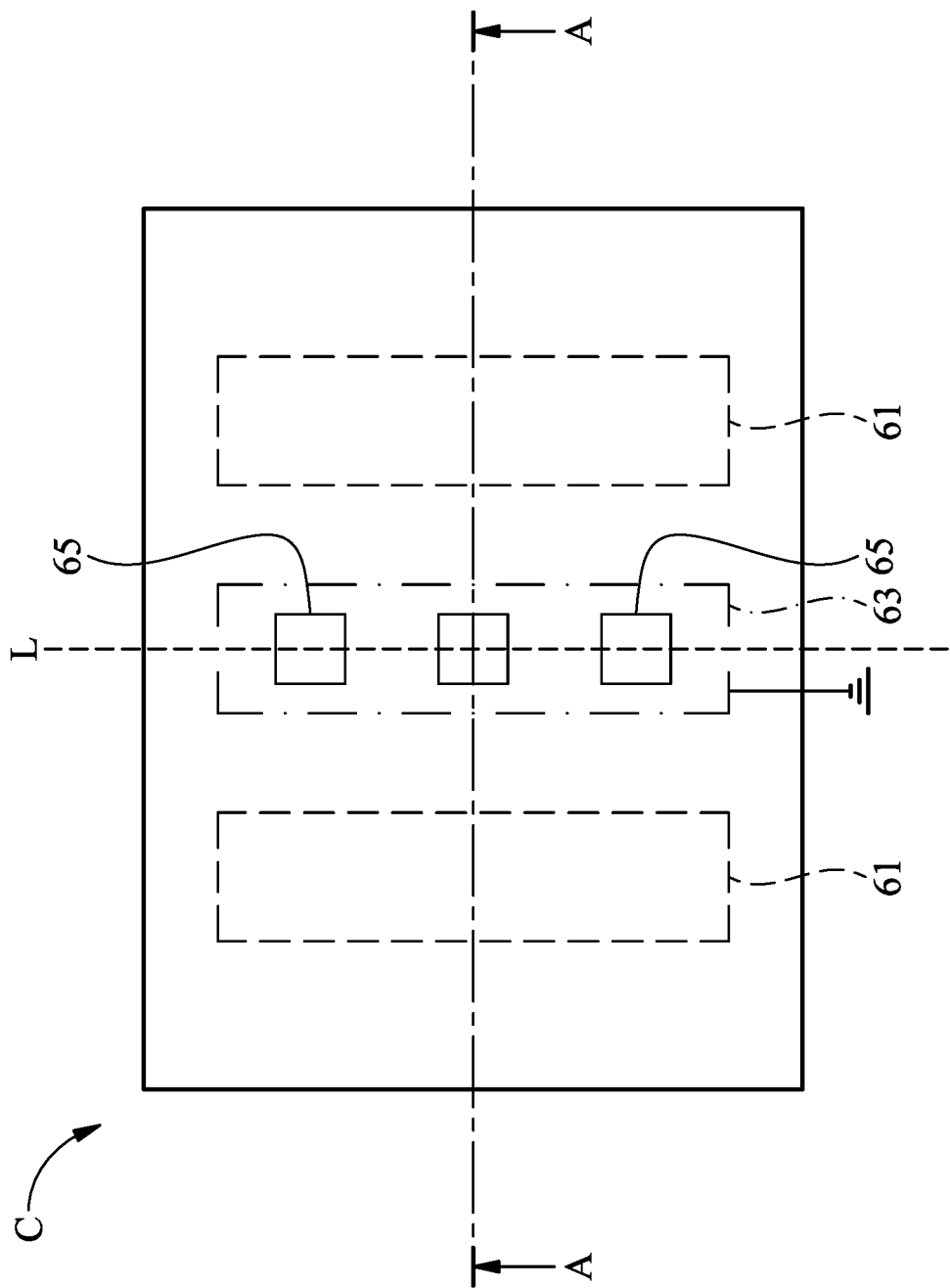
FIG. 5 is a plan view of a central test structure of a test key with sample features being centrally overlapped on a target feature, in accordance with some embodiments.

FIG. 5 shows a top view of the central test structure C, in accordance with some embodiments. In accordance with some embodiments, the central test structure C includes two reference features 61, a target feature 63, and a number of sample features 65. The two reference features 61 are positioned on two sides of the target feature 63. The sample features 65 are centrally located above the target feature 63. Namely, the center of each of the sample features 65 is arranged along a longitudinal line L of the target feature 63.

Figure 6A:
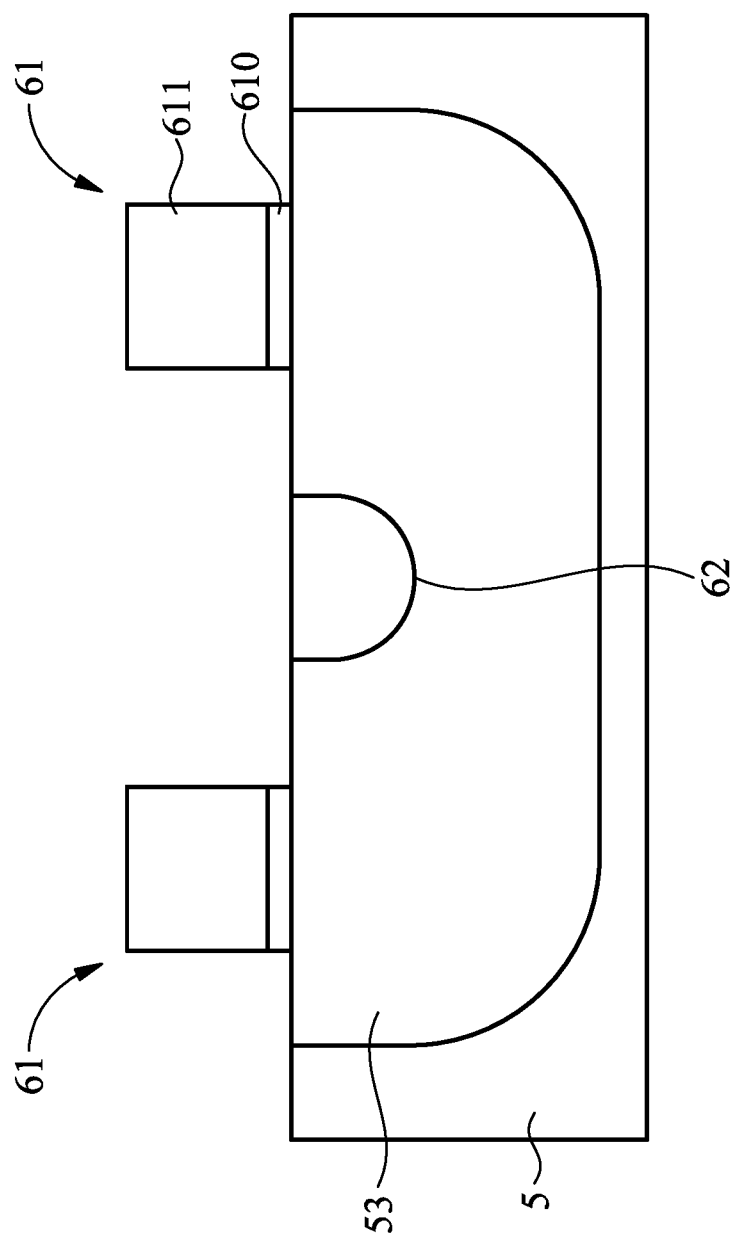
FIG. 6A is a cross-sectional view of one stage of a manufacturing process for forming a central test structure of a test key, in accordance with some embodiments.
Figure 6B:
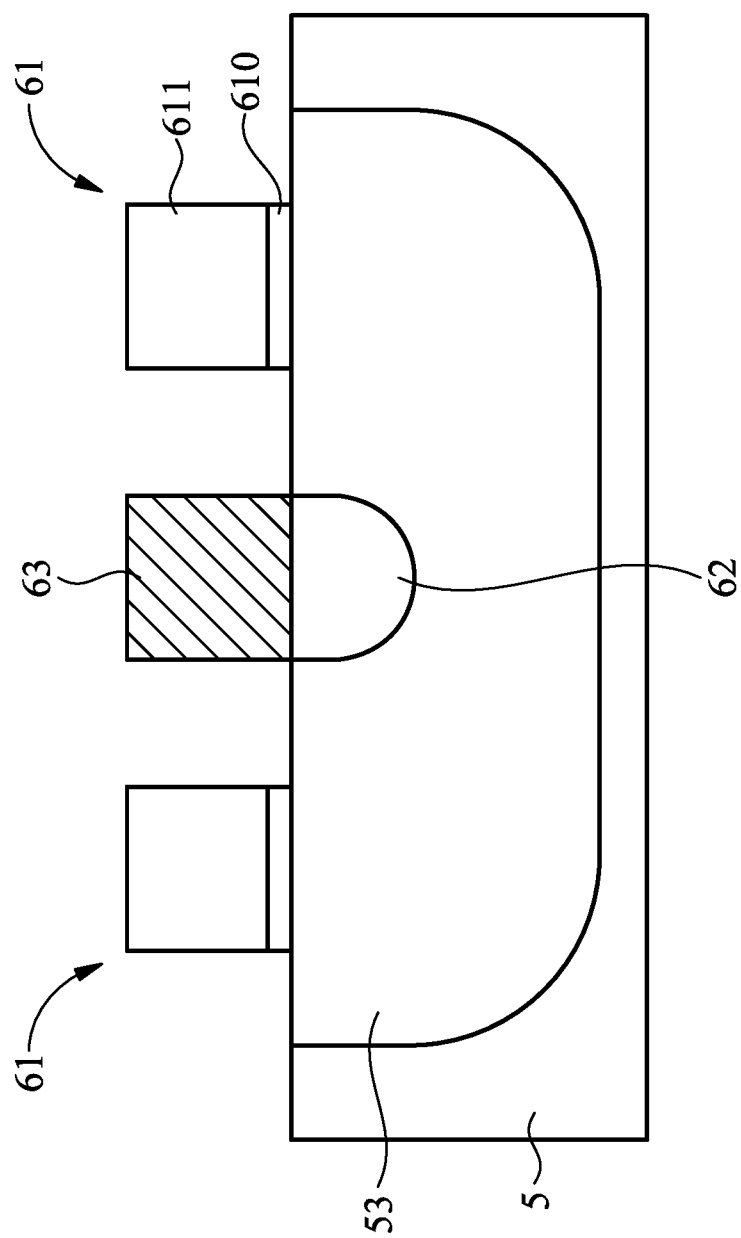
FIG. 6B is a cross-sectional view of one stage of a manufacturing process for forming a central test structure of a test key, in accordance with some embodiments.
Figure 6C:
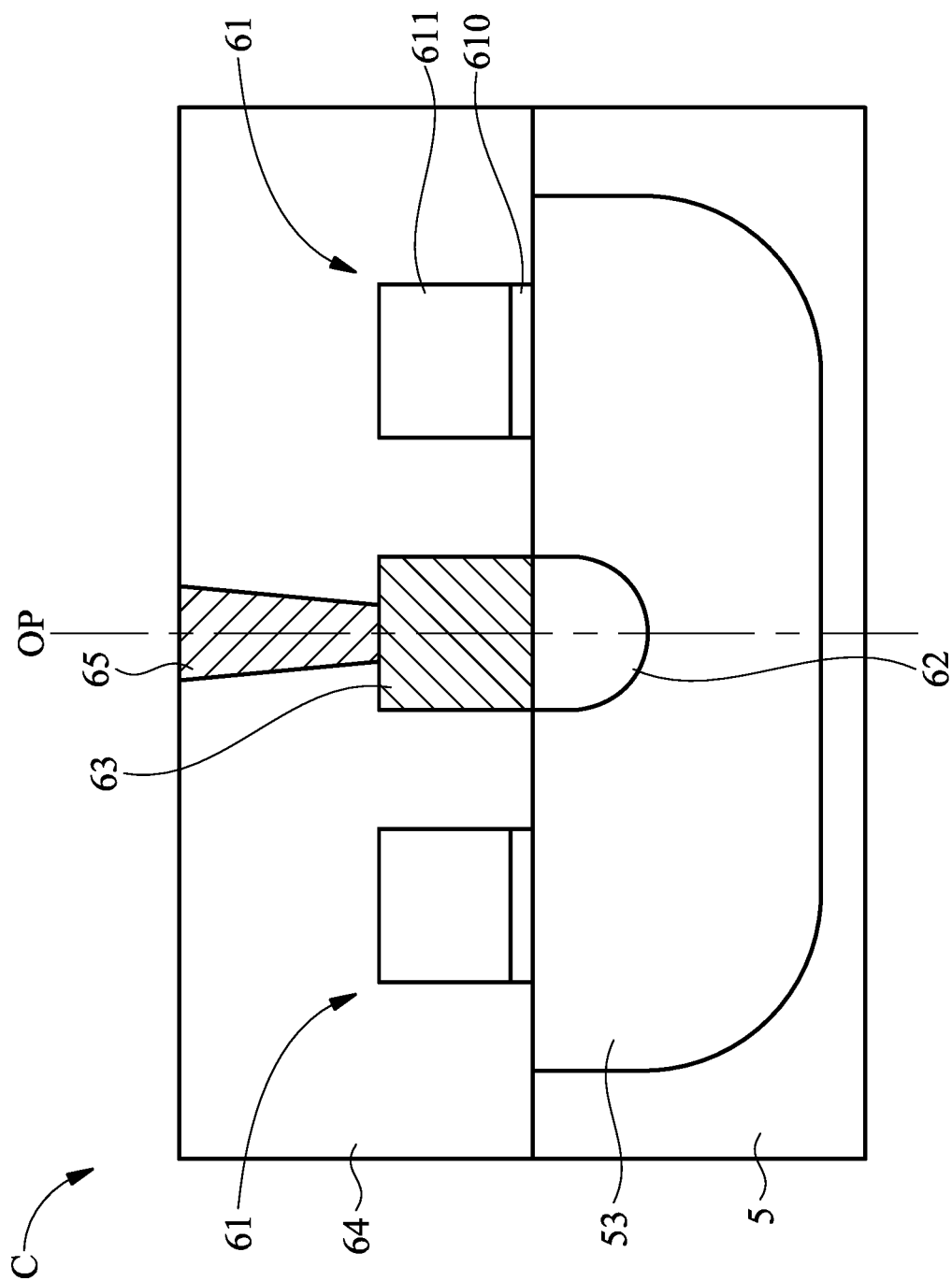
FIG. 6C is a cross-sectional view of one stage of a manufacturing process for forming a central test structure of a test key, in accordance with some embodiments.

FIGS. 6A-6C are cross-sectional views taken along line A-A of FIG. 5 of various stages of a process for forming the central test structure C, in accordance with some embodiments. As shown in FIG. 6A, a semiconductor wafer 5 is received or provided, in accordance with some embodiments. In some embodiments, the semiconductor wafer 5 is a bulk semiconductor substrate, such as a semiconductor wafer. For example, the semiconductor wafer 5 is a silicon wafer. The semiconductor wafer 5 may include silicon or another elementary semiconductor material such as germanium. In some other embodiments, the semiconductor wafer 5 includes a compound semiconductor. The compound semiconductor may include gallium arsenide, silicon carbide, indium arsenide, indium phosphide, another suitable material, or a combination thereof. In some embodiments, the semiconductor wafer 5 is an un-doped substrate. However, in some other embodiments, the semiconductor wafer 5 may be a doped substrate such as a P-type substrate.

In some embodiments, an N-well region 53 is formed in the semiconductor wafer 5, as shown in FIG. 6A. In some embodiments, an ion implantation process is performed to form the N-well region 53. N-type dopants such as phosphor or arsenic are implanted into the exposed portion of the semiconductor wafer 5 to form the N-well region 53. Afterwards, an annealing process is performed to drive in the implanted dopants in some embodiments. In some other embodiments, the N-well region is not formed if the semiconductor wafer 5 is an N-type semiconductor substrate.

As shown in FIG. 6A, the two reference features 61 are formed over the semiconductor wafer 5, in accordance with some embodiments. For example, in some embodiments of the present disclosure, the two reference features 61 are formed over the N-well region 53 of the semiconductor wafer 5. In some embodiments, each of the two reference features 61 includes a gate dielectric layer 610 over the N-well region 53 of the semiconductor wafer 5 and a gate electrode 611 over the gate dielectric layer 610.

In some embodiments, the gate dielectric layer 610 is made of silicon oxide, silicon nitride, silicon oxynitride, high-k material, any other suitable dielectric material, or a combination thereof. In some embodiments of the present disclosure, the high-k material may include, but is not limited to, metal oxide, metal nitride, metal silicide, transition metal oxide, transition metal nitride, transition metal silicide, transition metal oxynitride, metal aluminate, zirconium silicate, zirconium aluminate. For example, the material of the high-k material may include, but is not limited to, LaO, AlO, ZrO, TiO, $Ta_2O_5$, $Y_2O_3$, $SrTiO_3$(STO), $BaTiO_3$ (BTO), BaZrO, $HfO_2$, $HfO_3$, HfZrO, HfLaO, HfSiO, HfSiON, LaSiO, AlSiO, HfTaO, HfTiO, HfTaTiO, HfAlON, (Ba,Sr)$TiO_3$(BST), $Al_2O_3$, any other suitable high-k dielectric material, or a combination thereof.

In some embodiments, the gate electrode 611 is made of polysilicon, a metal material, another suitable conductive material, or a combination thereof. In some embodiments of the present disclosure, the metal material may include, but is not limited to, copper, aluminum, tungsten, molybdenum, titanium, tantalum, platinum, or hafnium. In some embodiments, the gate electrode 611 is a dummy gate electrode and will be replaced with another conductive material such as a metal material. The dummy gate electrode layer is made of, for example, polysilicon.

As shown in FIG. 6B, a source/drain region 62 is formed in the N-well region 53 of the semiconductor wafer 5, in accordance with some embodiments. In some embodiments, the source/drain region 62 is located between the two reference features 61 and in the semiconductor wafer 5. An implantation process is performed to form the source/drain region 62. In some embodiments, P-type dopants are implanted into the N-well region 53 to form the source/drain regions 62. Afterwards, an annealing process, such as a rapid thermal process (RTP), may be performed to repair the crystal structure of the silicon in the source/drain region 62 and activate the dopant in the source/drain region 62.

As shown in FIG. 6B, a target feature 63 is formed over the source/drain regions 62, in accordance with some embodiments. The target feature 63 may further decrease the on-resistance of the device. In some embodiments of the present disclosure, the target feature 63 includes a metal layer. In some embodiments, the metal silicide includes, but is not limited to, nickel silicide, cobalt silicide, tungsten silicide, titanium silicide, tantalum silicide, platinum silicide or erbium silicide.

As shown in FIG. 6C, a dielectric layer 64 is formed over the reference feature 61, in accordance with some embodiments. In some embodiments, a dielectric layer 64 is deposited to cover the source/drain region 62, the reference features 61 and the target feature 63. In some embodiments, the dielectric material layer includes silicon oxide, silicon oxynitride, borosilicate glass (BSG), phosphoric silicate glass (PSG), borophosphosilicate glass (BPSG), fluorinated silicate glass (FSG), low-k material, porous dielectric material, another suitable material, or a combination thereof. In some embodiments, the dielectric material layer is deposited using a CVD process, an ALD process, a spin-on process, a spray coating process, another applicable process, or a combination thereof.

Afterwards, the sample features 65 are formed in the dielectric layer 64 to form the central test structure C. As shown in FIG. 6C, the sample features 65 are electrically connected to the source/drain region 62. As shown in FIG. 6C, the sample features 65 are in direct contact with the target feature 63 over the source/drain regions 62, in accordance with some embodiments.

In some embodiments of the present disclosure, the sample features 65 are made of a single layer or multiple layers of copper, aluminum, tungsten, gold, chromium, nickel, platinum, titanium, iridium, rhodium, an alloy thereof, a combination thereof, or any other conductive material.

In some embodiments of the present disclosure, openings are formed in the dielectric layer 64 to expose the target feature 63. In some embodiments, the formation of the openings includes patterning the dielectric layer 64 by a photolithography process, etching the exposed surface of the dielectric layer 64 (for example, by using a dry etching process, a wet etching process, a plasma etching process, or a combination thereof) to form the openings.

Afterwards, a conductive material layer is deposited over the dielectric layer 64 and fills into the openings. In some embodiments, the conductive material layer is deposited by using chemical vapor deposition (CVD), sputtering, resistive thermal evaporation, electron beam evaporation, or any other suitable methods.

Afterwards, a planarization process may be used to partially remove the conductive material layer. The conductive material layer may be partially removed until the dielectric layer 64 is exposed. As a result, the conductive material layer that remains in the openings forms the sample features 65. In some embodiments, the planarization process includes a CMP process, a grinding process, a dry polishing process, an etching process, another applicable process, or a combination thereof.

In some embodiments, each of the first group of test structures R1, R2 . . . R9 and R10 and the second group of test structures L1, L2 . . . L9 and L10 includes two reference features 61, a target feature 63, and a number of sample features 65. The method for forming the two reference features 61, the target feature 63 and the sample feature 65 in each test structure is similar to that of the central test structure C. However, the offset distance between the sample feature 65 and the target feature 63 of each of the test structures is not equal to zero.

Figure 7:
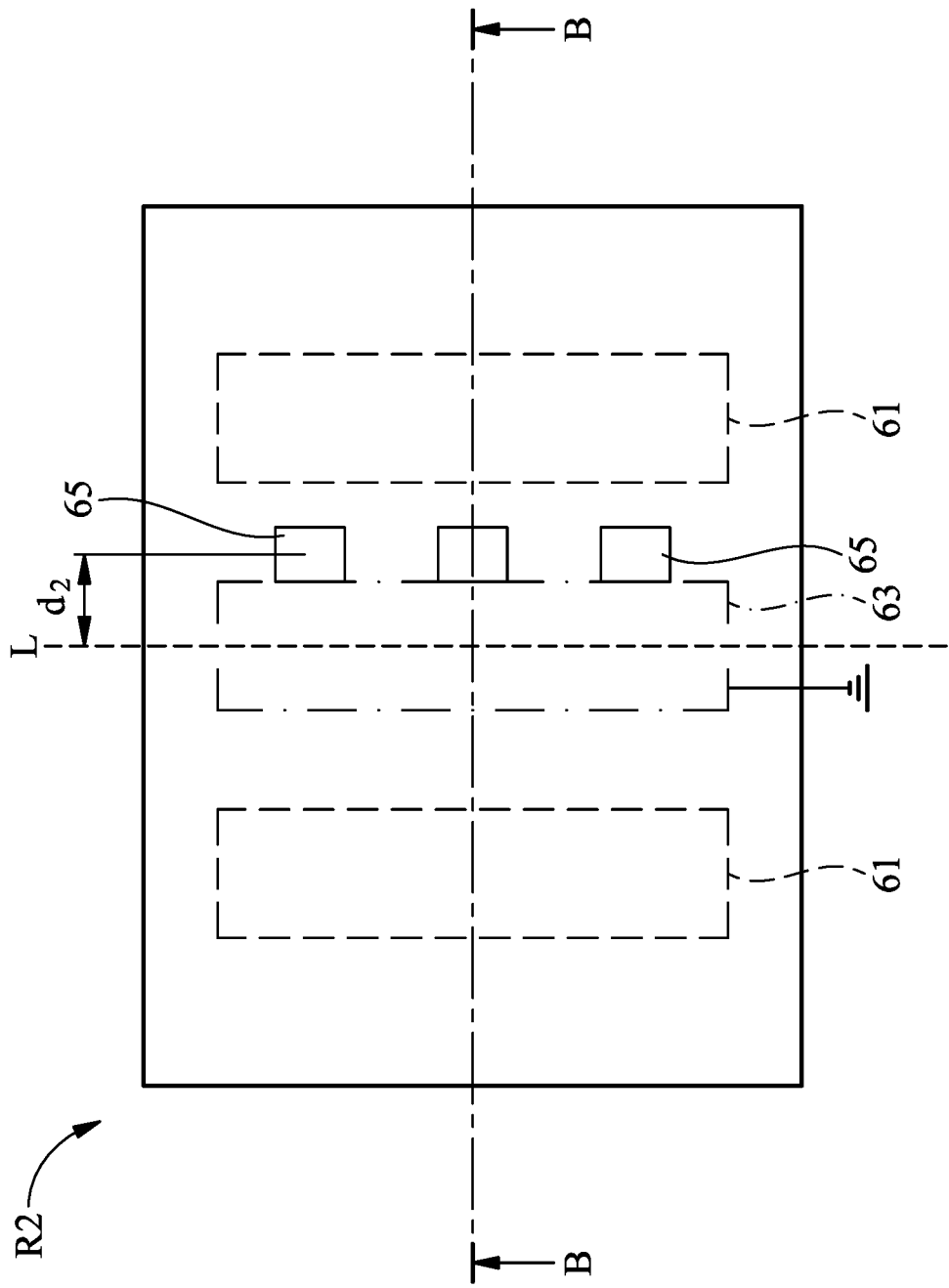
FIG. 7 is a plan view of a test structure with sample features with sample features being offset from a target feature, in accordance with some embodiments.
Figure 8:
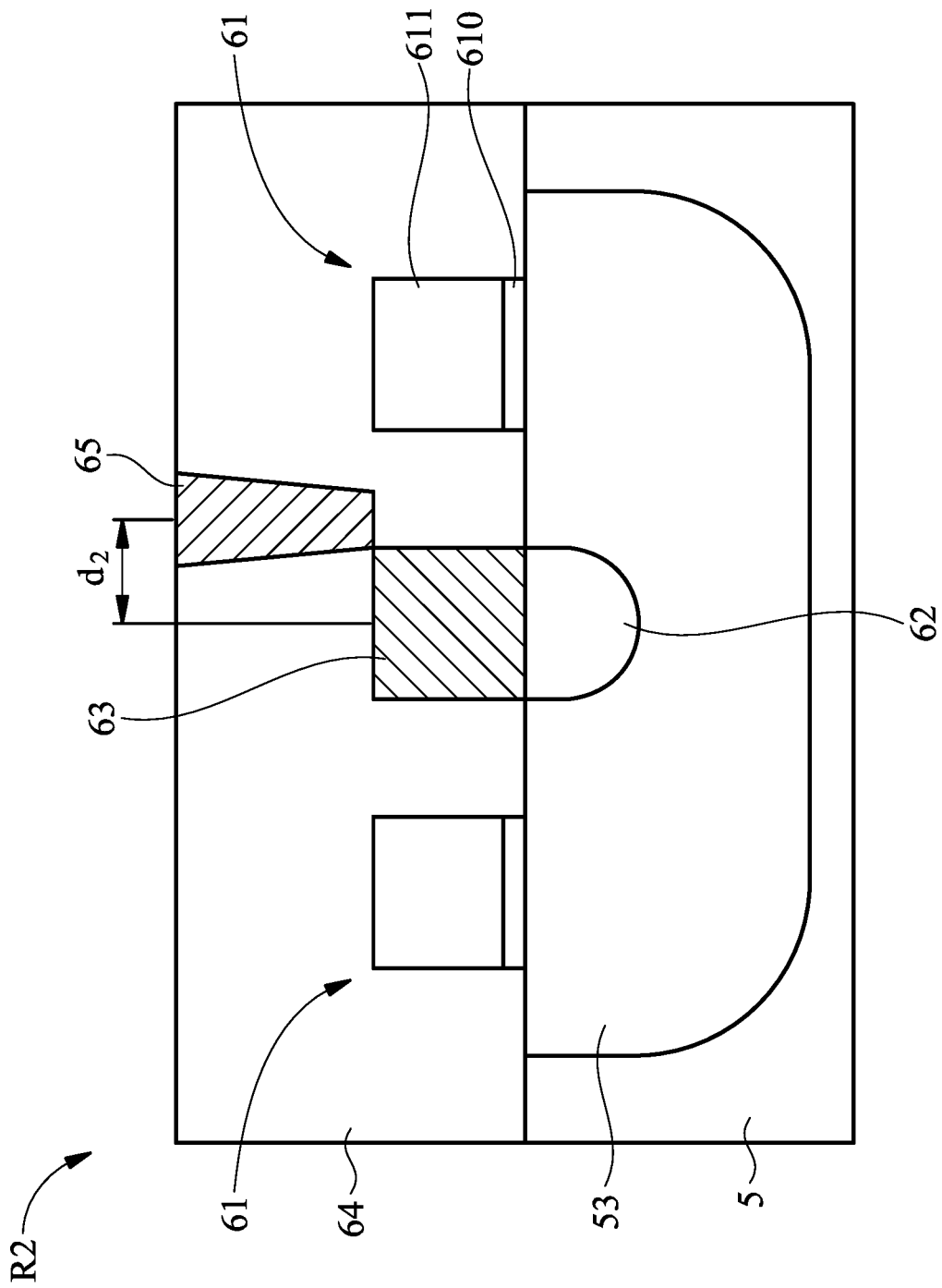
FIG. 8 is a cross-sectional view of a test structure with sample features being offset from a target feature.

For example, as shown in FIGS. 7 and 8, the test structure R2 includes two reference features 61, a target feature 63, and a number of sample features 65. Configurations of the test structure R2 are similar to that of central test structure C, and differences between the test structure R2 and the central test structure C include the sample feature 65 of the test structure R2 not being centrally located on the target feature 63. The center of each of the sample features 65 of the test structure R2 is distant from the longitudinal line L of the target feature 63 by an offset distance $d_2$.

In some embodiments, the offset distance between the sample feature 65 and the target feature 63 of each of the test structures increases gradually along the two different directions D1 and D2. That is distance between the sample feature 65 and the reference feature 62 of each of the test structure decreases gradually along the two directions D1 and D2.

For example, referring back to FIG. 4, the offset distance between the sample feature 65 and the target feature 63 of the test structure R1 in the first direction D1 is about 1 nanometer. The offset distance between the sample feature 65 and the target feature 63 of the test structure R2 in the first direction D1 is about 2 nanometers. The offset distance between the sample feature 65 and the target feature 63 of the test structure R9 in the first direction D1 is about 9 nanometers. The offset distance between the sample feature 65 and the target feature 63 of the test structure R10 in the first direction D1 is about 10 nanometers.

In some embodiments, the offset distance $d_n$ of the test structure in the first group satisfies with the equation $d_n = n \ast d_0$, where n is the order of the test structure in the first group of test structure counted from the central test structure C, and $d_0$ is a unit offset distance between the test structure R1 and the central test structure C. For the test structure R2, n is equal to 2 and thus the offset distance $d_2$ equals two times d0.

In some embodiments, there is a unit offset distance which may be about 1 nm. However, it should be appreciated that many variations and modifications can be made to embodiments of the disclosure. The unit offset distance (i.e., the difference between the offset distances in two neighboring test structures) may be varied as long as a user or a computer can discriminate between the brightness (or gray levels) of two images of two neighboring test structures. In some other embodiments, the difference between the offset distances in two neighboring test structures increases gradually in a direction away from the central test structure C.

The arrangement of the second group of test structures is similar to that of the first group of test structures. The offset distance between the sample feature 65 and the target feature 63 of the test structure L1 in the second direction D2 is about 1 nanometer. An offset distance between the sample feature 65 and the target feature 63 of the test structure L2 in the second direction D2 is about 2 nanometers. An offset distance between the sample feature 65 and the target feature 63 of the test structure L9 in the second direction D2 is about 9 nanometers. An offset distance between the sample feature 65 and the target feature 63 of the test structure L10 in the second direction D2 is about 10 nanometers.

In some embodiments, the offset distance $d_n$ in the second direction D2 of the test structure in the second group satisfies with the equation $d_n = n \ast d_0$, where n is the order of the test structure in the second group of test structure counted from the central test structure C, and $d_0$ is a unit offset distance between the test structure L1 and the central test structure C. For the test structure L2, n is equal to 2 and thus the offset distance $d_2$ equals two times $d_0$.

The method 70 also includes operation 72, in which an image of the test structures of the test key 60 is produced by scanning an electron beam over the test key 60. In some embodiments, operation 72 is performed after formation of the first layer M1 (FIG. 2) including the test key 60 are finished. In some embodiments, operation 72 is performed before formation of a next layer, such as the second layer M2, which is deposited over the first layer M1.

In some embodiments, operation 72 is executed in the wafer inspecting apparatus 1 shown in FIG. 1. The semiconductor wafer 5 may be moved from an apparatus which executes the last process in operation 71 to the wafer inspecting apparatus 1.

For example, the semiconductor wafer 5 is moved from a CMP apparatus (not shown in figures) to the wafer inspecting apparatus 1 and positioned on the wafer stage assembly 30. In some embodiments, the semiconductor wafer 5 is mounted on the wafer holder 32 by a clamping mechanism, such as vacuum clamping or e-chuck clamping. In some embodiments, after the semiconductor wafer 5 is positioned on the wafer holder 32, a working distance between the objective lens 26 and a process surface (top surface) of the semiconductor wafer 5 is adjusted by driving the actuator 31 to move the wafer holder 32 up and down.

In some embodiments, an image region where the test key 60 is located is designated on the semiconductor wafer 5. The shape of the image region is rectangular and an area of the image region is in a range from about 0.04 mm$^2$ to about 5.7 mm$^2$. However, it should be appreciated that many variations and modifications can be made to embodiments of the disclosure. The image region may be any other shape according to demand.

To produce the images of a portion of the selected image region, a scanning operation is performed by the image capturing assembly 20. In the beginning of the scanning operation, focus is set at the beginning as the recipe. Both the objective lens 26 and the wafer stage assembly 30 are adjusted to make sure the focus is good. Afterwards, the charged particle beam 2 produced by the image capturing assembly 20 is driven to scan the selected image region. After the whole area of the selected image region is scanned by the charged particle beam 2, an image (e.g., voltage contract (VC) image) of the selected image region including the test key 60 is displayed and recorded by the image processing assembly 40.

In some embodiments, the gray level or brightness of the image of the sample features 65 in the test structures is a function of the electrical conductivity of the sample feature 65. The larger contact area formed between the sample feature 65 and the target feature 63 leads to a smaller electrical resistivity of the sample feature 65, i.e., a greater electrical conductivity. In the test structures, the electrical resistivity of the sample features 65 increases as the respective offset distance $d_n$ between the sample feature 65 and the target feature 63 increases.

In addition, since the target feature 63 is electrically grounded via the N-well region 53 and the reference features 61 are electrically insulated, when an electron beam impinges on the test structures, the images of the test structures show different gray levels or brightness.

Specifically, as shown in FIG. 4, images of the sample features 65 having higher electrical resistivity appear relatively dark, and images of the sample features 65 having lower electrical resistivity appear relatively bright. Therefore, as shown in FIG. 4, the central test structure C has the highest gray level or brightness, and the test structures R10 and L10 have the lowest gray level or brightness. In addition, the gray level or brightness gradually decreases along the directions D1 and D2 from that of the central test structure C.

The method 70 also includes operation 73, in which an image analysis of the image is performed to determine if a defect has occurred.

In some embodiments, an overlay error is monitored by analyzing the VC image produced from the image capturing assembly 20 to determine if a defect has occurred. In accordance with some embodiments, the operation for monitoring the overlay error includes recognizing the contour of the test key 60 in the VC image by suitable image segmentation technology, such as thresholding image processing technology. The operation for monitoring the overlay error further includes calculating the gray level (or brightness) of each of the pixels of the image of the test key 60. The operation for monitoring the overlay error also includes determining a current center position at which the image has the highest gray level (or brightness).

In addition, the operation for monitoring the overlay error includes calculating a distance between the current center position and a theoretic center position. The theoretic center position may be data associated a coordinate in the VC image where the central test structure C should be located. Namely, if the central test structure C is located at the theoretic center position, the overlay error is equal to zero. The data associated with the theoretic center position may be recorded in a database and sent to the signal processor 41 once the image region is selected.

Figure 9:
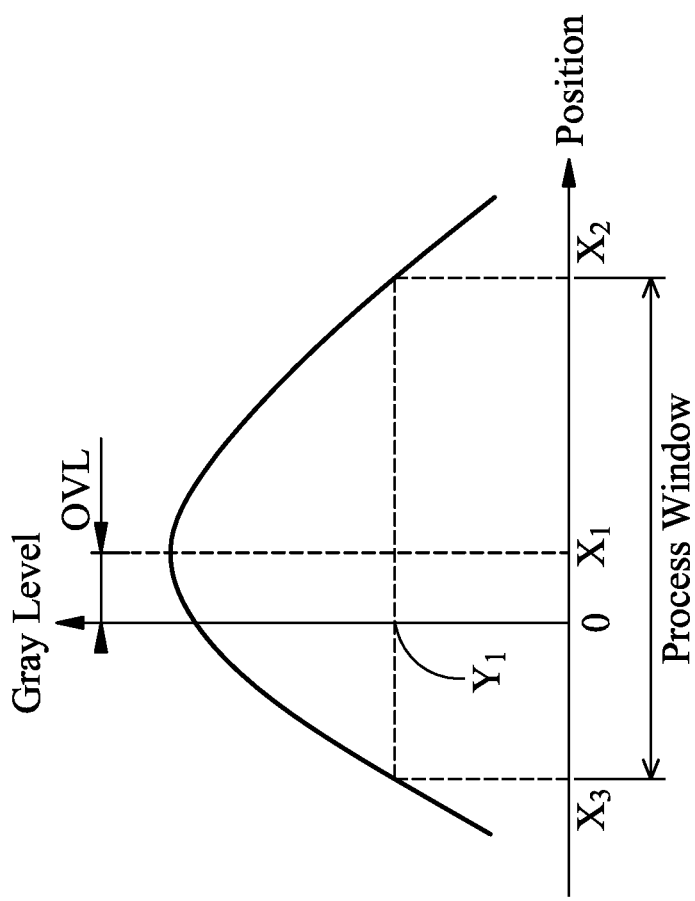
FIG. 9 is a diagram showing the results of an image analysis of a test key, in accordance with some embodiments.

For example, as shown in FIG. 9, the result of the image analysis indicates that the current center position $X_1$ has the highest gray level (or brightness), and the origin of the coordinates shown in diagram of FIG. 9 represents the theoretic center position. By calculating the distance between the current center position $X_1$ and the theoretic center position, the overlay error OVL of the test key 60 is obtained.

In some other embodiments, a process window is monitored by analyzing the VC image produced from the image capturing assembly 20 to determine if a defect occurs. The process window is a collection of values of process parameters that allow circuit to be manufactured under desired specifications. In one example, the process window for the critical dimension (CD) is considered to ensure the CD is in the desired range. A wider process window means the process allows higher deviation in lithography parameters, and the product yield can be improved.

In accordance with some embodiments, the operation for monitoring the process window includes recognizing the contour of the test key 60 in the VC image by suitable image segmentation technology, such as thresholding image processing technology. The operation for monitoring the process window further includes calculating the gray level (or brightness) of each of the pixels of the image of the test key 60. In addition, the operation for monitoring the process window also includes retrieving two boundary positions which manifest a particular gray level (or brightness).

For example, as shown in FIG. 9, the result of the image analysis indicates that positions $X_2$ and $X_3$ has the particular gray level (or brightness) $Y_1$. By calculating the distance between the positions $X_2$ and $X_3$, the process window of the test key 60 is obtained.

Since there is a correlation between the gray level and the electrical characteristic of the sample features 65, the test structures located within the two boundary positions (i.e. having a higher gray level than the particular gray level) may exhibit acceptable electrical characteristics. Conversely, the test structures located outside of the two boundary positions may show unacceptable electrical characteristics.

The method 70 also includes operation 74, in which the results of image analysis are compared with preset criteria to determine if the obtained overlay error and/or the process window are acceptable. When the obtained overlay error within a tolerable range, such as the range defined in the production specification, the method 70 may proceed to subsequent operation 76. In operation 76, as shown in FIG. 4, another layer M2 may be formed over the layer M1. The layer M2 may have its own test key formed therein, and the method 70 repeats operations 72 to 74. For example, the test key 60 in the layer M2 includes a number of test structures, such as the central test structure C, the first group of test structures R1, R2 . . . R9 and R10, and the second group of test structures L1, L2 . . . L9 and L10. The central test structure C is positioned in an original position OP.

Conversely, when the obtained overlay error is outside of a tolerable range, the method 70 proceeds to operation 75 (FIG. 3), in which a warning is issued. The warning may be indicative a misalignment of two stacked features in the wafer dies, and the semiconductor may be discarded without further processing for the sake of reducing the manufacturing cost.

The process window is related to the critical dimension (CD) of the sample feature 65 and the overlay error. When the overlay error is within an acceptable range but the process window is smaller than a process window criterion, a defect is diagnosed and the method 70 proceeds to operation 75. Conversely, when the process window is greater than a process window criterion, the method 70 may proceed to subsequent operation 76.

Figure 10:
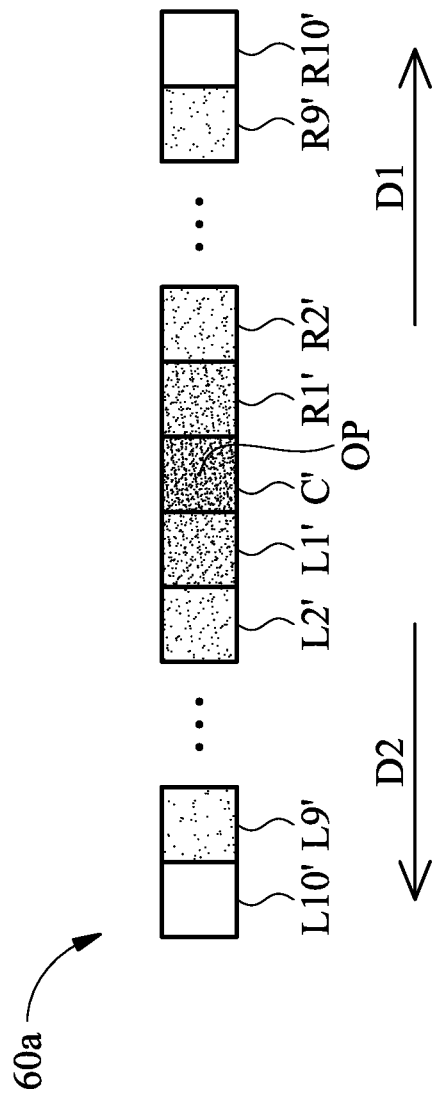
FIG. 10 is a schematic view of a test key, in accordance with some embodiments.

FIG. 10 shows a schematic view of a test key 60a, in accordance with some embodiments. In some embodiments, the test key 60a includes a number of test structures, such as central test structure C', first group of test structures R1', R2' . . . R9' and R10', and second group of test structures L L2' . . . L9' and L10'. The central test structure C' is positioned in the original position OP.

The first group of test structures R1', R2' . . . R9' and R10' are arranged in order along the first direction D1 from the original position OP. Specifically, the test structure R1' is positioned at a side of the central test structure C in the first direction D1. The test structure R2' is positioned at a side of the test structure R1' in the first direction D1. The test structure R9' is positioned at a side of the test structure R2' in the first direction D1. Another six test structures (not shown in figures) are positioned between the test structure R2 and the test structure R9'. The test structure R10' is positioned at a side of the test structure R9' in the first direction D1.

In some embodiments, two neighboring test structures of the first group of test structures R1', R2' . . . R9' and R10' are directly connected to each other. However, it should be appreciated that many variations and modifications can be made to embodiments of the disclosure. In some other embodiments, two neighboring test structures of the first group of test structures R1', R2' . . . R9' and R10' are distant away from each other by a predetermined width.

The second group of test structures L1', L2' . . . L9' and L10' are arranged in order along the second direction D2' from the original position OP. The second direction D2 is opposite to the first direction D1. Specifically, the test structure L1' is positioned at the side of the central test structure C in the second direction D2. The test structure L2' is positioned at a side of the test structure L1' in the second direction D2. The test structure L9' is positioned at a side of the test structure L2' in the second direction D2. Another six test structures (not shown in figures) are positioned between the test structure L2' and the test structure L9'. The test structure L10' is positioned at a side of the test structure L9' in the second direction D2.

In some embodiments, two neighboring test structures of the second group of test structures L1', L2' . . . L9' and L10' are directly connected to each other. However, it should be appreciated that many variations and modifications can be made to embodiments of the disclosure. In some other embodiments, two neighboring test structures of the second group of test structures L1', L2' . . . L9' and L10' are distant away from each other by a predetermined width.

The differences between the test key 60a and the test key 60 include the reference features 61 being electrically grounded, and the target features 63 being electrical insulated.

Figure 11:
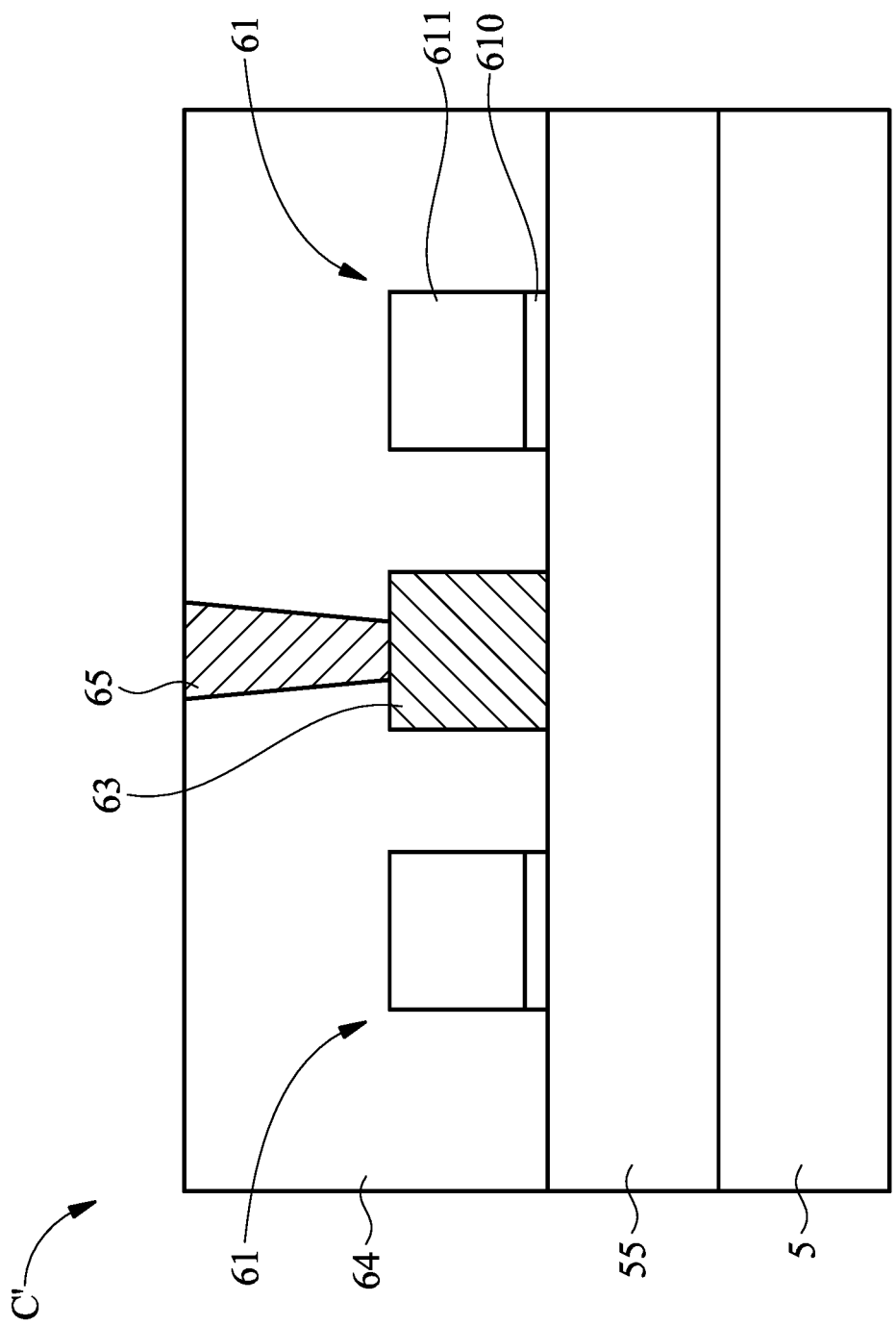
FIG. 11 is a cross-sectional view of a central test structure with sample features being centrally overlapped on a target feature, in accordance with some embodiments.

For example, as shown in FIG. 11, the central test structure C' includes two reference features 61, a target feature 63, and a number of sample features 65. The target features 63 may be electrically insulated by an underlying STI (Shallow Trench Isolation) structure 55. The sample features 65 are centrally located above the target feature 63. The two reference features 61 are positioned on two sides of the target feature 63.

Figure 12:
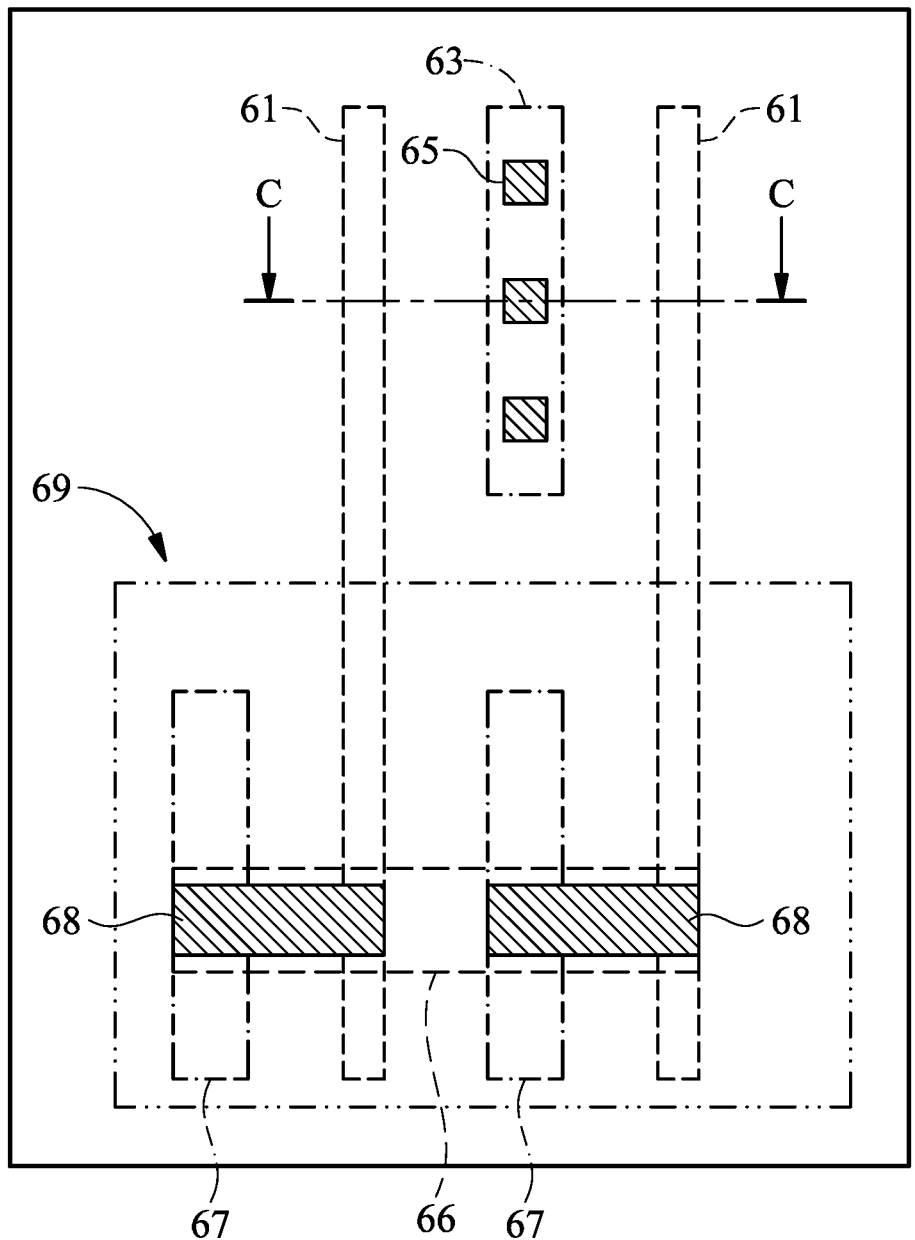
FIG. 12 is a plan view of a central test structure, in accordance with some embodiments, wherein reference features are electrical grounded via an N-well region.

FIG. 12 shows a plan view of the central test structure C'. In some embodiments, the central test structure C' further includes an N-well region 69. The two reference features 61 are electrically grounded via the N-well underlying region 69. Specifically, a fin member 66 is formed in the N-well underlying region 69, and two ground features 67 are formed on the fin member 66. The two reference features 61 extend into the N-well underlying region 69. Each of the two reference features 61 is electrically connected to the ground feature 67 via a metal line 68 formed over the reference feature 61 and the ground feature 67.

Figure 13:
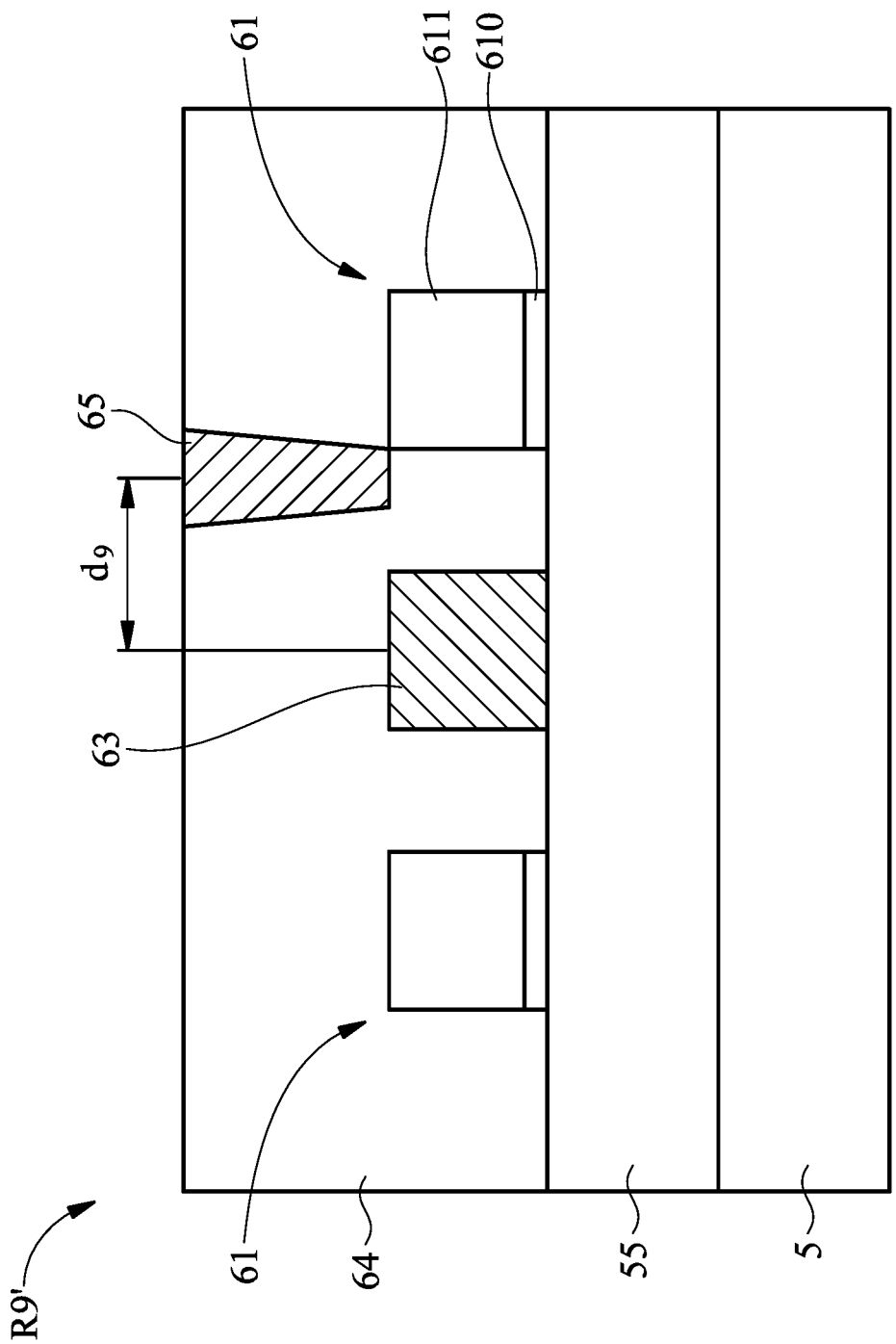
FIG. 13 is a cross-sectional view of a test structure with sample features being offset from a target feature, in accordance with some embodiments.

Configurations of the test structures R1', R2' . . . R9' and R10' and test structures L1', L2' . . . L9' and L10' are similar to that of the central test structure C', but the offset distance between the sample feature 65 and the target feature 63 of each of the test structures increases gradually along the two different directions D1 and D2. For example, as shown in FIG. 13 the center of sample feature 65 of the test structure R9 is distant from the center of the target feature 63 by an offset distance $d_9$.

By implementing the method 70 to inspect the test key 60a, an overlay error and a process window can be obtained. An image of the test key 60a produced by the image capturing assembly 20 in operation 72 may be shown in FIG. 10. Due to the difference of electrical characteristic, the central test structure C' has the lowest gray level or brightness, and the test structures R10' and L10' have the highest gray level or brightness. In addition, the gray level or brightness gradually increases along the directions D1 and D2 from that of the central test structure C'.

Figure 14:
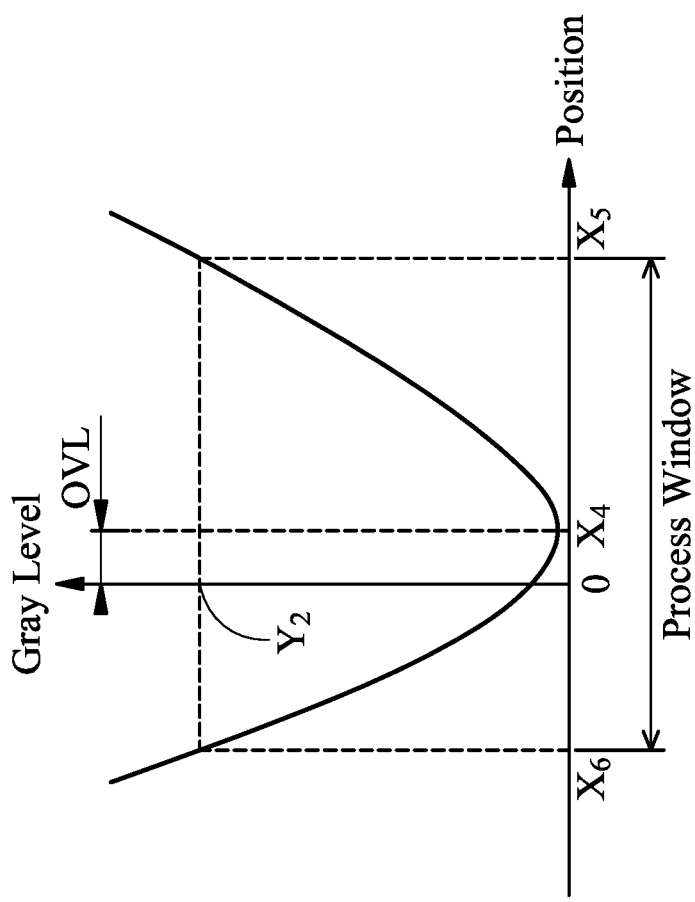
FIG. 14 is a diagram showing the results of an image analysis of the test key, in accordance with some embodiments.

A result of the image analysis of the image of the test key 60a may be shown as the diagram of FIG. 14. The overlay error of the test key 60a can be obtained by determining a current center position at which the image has the lowest gray level and calculating a distance between the current center position and a theoretic center position. For example, as shown in FIG. 14, the result of the image analysis indicates that the position $X_4$ has the lowest gray level (or brightness), and the origin of the coordinates shown in diagram of FIG. 14 represents the theoretic center position. By calculating the distance between the position $X_4$ and the theoretic center position, the overlay error OVL of the test key 60a is obtained.

In addition, the process window of the test key 60a can be obtained by retrieving two boundary positions which manifest a particular gray level and calculating the length between the two boundary positions. For example, as shown in FIG. 14, the result of the image analysis indicates that positions $X_5$ and $X_6$ has the particular gray level (or brightness) $Y_2$. By calculating the distance between the position $X_5$ and $X_6$, the process window of the test key 60 is obtained.

In operation 74, when the obtained overlay error is within a tolerable range and/or the process window is larger than a process window criterion, the method 70 may proceed to subsequent operation 76, otherwise a warning is issued and the method 70 proceeds to operation 75, in which a warning is issued. The warning may be indicative a misalignment of two stacked features in the wafer dies, and the semiconductor may be discarded without further processing for the sake of reducing the manufacturing cost.

Embodiments of method and apparatus for monitoring in-line process state utilized an electron beam to image a test key formed in the semiconductor wafer. The test key includes a number of test structures each manifests different gray levels in the voltage contrast image. By analyzing the voltage contrast image an overlay error and process window can be determined. Since the overlay error and process window are monitored after the completion of each layer, processing problems can be quickly identified and solved. As a result, the manufacturing cost is reduced. On the other hand, due to superior image quality and deviation of the voltage contrast image, overlay error and process window can be accurately monitored in the comparison of a conventional method which uses optical images to determine the critical dimension and overlay error.

In accordance with some embodiments, a method for inline inspection during semiconductor wafer fabrication is provided. The method includes forming a number of test structures on a semiconductor wafer along two opposite directions. Each of the test structures includes a target feature and a sample feature formed over the target feature. An offset distance between the sample feature and the target feature of each of the test structures increases gradually along the two opposite directions. The method further includes producing an image of the test structures by applying an electron beam over the test structures. The method also includes performing image analysis of the image to recognize a current center position at which a minimum gray level or a maximum gray level is displayed. In addition, the method includes calculating an overlay error according to the current center position.

In accordance with some embodiments, a method for inline inspection during semiconductor wafer fabrication is provided. The method includes forming a number of test structures on a semiconductor wafer along two opposite directions. Each of the test structures includes a target feature and a sample feature formed over the target feature. An offset distance between the sample feature and the target feature of each of the test structures increases gradually along the two opposite directions. The method further includes producing an image of the test structures by applying an electron beam over the test structures. The method also includes performing image analysis of the image to recognize two boundary positions at which a particular gray level is displayed. In addition, the method includes calculating a process window according to the boundary positions.

In accordance with some embodiments, an apparatus for inspecting a semiconductor wafer is provided. The semiconductor wafer includes a number of test structures arranged along two opposite directions. Each of the test structures includes a target feature and a sample feature formed over the target feature, and an offset distance between the sample feature and the target feature of each of the test structures increases gradually along the two opposite directions. The apparatus includes a stage assembly configured to hold the semiconductor wafer. The apparatus further includes a charged particle source positioned over the stage and configured to emit an electron beam over the test structures. The apparatus also includes an electron detector positioned on the stage assembly. The electron detector is configured to receive secondary electrons from the test structures and produce images according to the detected secondary electrons. In addition, the apparatus includes a signal processor connected to the image producer. The signal processor is configured to recognize a current center position at which a minimum gray level or a maximum gray level is displayed in the image.

Although the embodiments and their advantages have been described in detail, it should be understood that various changes, substitutions, and alterations can be made herein without departing from the spirit and scope of the embodiments as defined by the appended claims. Moreover, the scope of the present application is not intended to be limited to the particular embodiments of the process, machine, manufacture, composition of matter, means, methods, and steps described in the specification. As one of ordinary skill in the art will readily appreciate from the disclosure, processes, machines, manufacture, compositions of matter, means, methods, or steps, presently existing or later to be developed, that perform substantially the same function or achieve substantially the same result as the corresponding embodiments described herein may be utilized according to the disclosure. Accordingly, the appended claims are intended to include within their scope such processes, machines, manufacture, compositions of matter, means, methods, or steps. In addition, each claim constitutes a separate embodiment, and the combination of various claims and embodiments are within the scope of the disclosure.

What is claimed is:

1. A method for inspection during semiconductor wafer fabrication, comprising:
   forming a plurality of test structures on a semiconductor wafer along two opposite directions, wherein each of the test structures comprises a target feature and a sample feature formed over the target feature, wherein an offset distance between the sample feature and the target feature of each of the test structures increases gradually along the two opposite directions, wherein each of the test structures further comprises a reference feature beneath the sample feature and adjacent to the target feature, wherein a distance between the sample feature and the reference feature of each of the test structures decreases gradually along the two opposite directions;
   producing an image of the test structures by applying an electron beam over the test structures;
   performing image analysis of the image to recognize a current center position at which a minimum gray level or a maximum gray level is displayed; and
   calculating an overlay error according to the current center position.

2. The method as claimed in claim 1, wherein calculation of the overlay value comprises calculating a distance between a theoretic center position and the current center position.

3. The method as claimed in claim 1, further comprising issuing a warning when the overlay error is outside of a tolerable range.

4. The method as claimed in claim 1, further comprising connecting the reference features to ground and electrically insulating the target feature;
   wherein the current center position has the minimum gray level in the image of the test structure.

5. The method as claimed in claim 1, further comprising connecting the target feature to ground; and
   wherein the current center position has the maximum gray level in the image of the test structure.

6. The method as claimed in claim 1, wherein the test structures comprises a central test structure located at an original position, and the other test structures are arranged along the two opposite directions from the original position, the target feature of the central test structure centrally overlaps the corresponding sample feature.

7. The method as claimed in claim 1, wherein a gray level of the image of the sample features in the test structures is a function of an electrical conductivity of the sample features, and a contact area formed between each of the sample feature and the respective target feature changes the electrical conductivity of the sample feature.

8. The method as claimed in claim 1, wherein two neighboring test structures of the test structures are directly connected to each other.

9. The method as claimed in claim 1, wherein two neighboring test structures of the test structures are distant away from each other by a predetermined width.

10. A method for inspection during semiconductor wafer fabrication, comprising:
    forming a plurality of test structures on a semiconductor wafer along two opposite directions, wherein each of the test structures comprises a target feature and a sample feature formed over the target feature, wherein an offset distance between the sample feature and the target feature of each of the test structures increases gradually along the two opposite directions, wherein each of the test structures further comprises a reference feature beneath the sample feature and adjacent to the target feature, wherein a distance between the sample feature and the reference feature of each of the test structures decreases gradually along the two opposite directions;

producing an image of the test structures by applying an electron beam over the test structures;

performing image analysis of the image to recognize two boundary positions at which a particular gray level is displayed; and calculating a process window according to the two boundary positions.

11. The method as claimed in claim 10, wherein calculation of the process window comprises calculating a length between the two boundary positions.

12. The method as claimed in claim 10, further comprising issuing a warning when the process window is less than a process window criterion.

13. The method as claimed in claim 10, further comprising connecting the reference features to ground and electrically insulating the target feature;

wherein the current center position has a minimum gray level in the image of the test structures.

14. The method as claimed in claim 10, further comprising connecting the target feature to ground; and wherein the current center position has a maximum gray level in the image of the test structures.

15. The method as claimed in claim 10, wherein the test structures comprise a central test structure located at an original position, and the other test structures are arranged along the opposite directions from the original position, the target feature of the central test structure centrally overlaps the corresponding sample feature.

16. The method as claimed in claim 10, wherein a gray level of the image of the sample features in the test structures is a function of an electrical conductivity of the sample features, and a contact area formed between each of the sample feature and the respective target feature changes the electrical conductivity of the sample feature.

17. A wafer inspecting apparatus for inspecting a semiconductor wafer comprising:

a plurality of test structures arranged along two opposite directions, wherein each of the test structures comprises a target feature and a sample feature formed over the target feature, wherein an offset distance between the sample feature and the target feature of each of the test structures increases gradually along the two opposite directions, wherein each of the test structures further comprises a reference feature beneath the sample feature and adjacent to the target feature, wherein a distance between the sample feature and the reference feature of each of the test structures decreases gradually along the two opposite directions, the apparatus comprising:

a stage assembly configured to hold the semiconductor wafer;

a charged particle source positioned over the stage assembly and configured to emit an electron beam over the test structures;

a detector positioned over the stage assembly and configured to receive secondary electrons from the test structures and produce image according to the detected secondary electrons; and a signal processor connected to the detector and configured to recognize a current center position at which a minimum gray level or a maximum gray level is displayed in the image.

18. The apparatus as claimed in claim 17, wherein the signal processor is also configured to recognize two boundary positions at which a particular gray level are displayed in the image.

19. The apparatus as claimed in claim 17, wherein the reference features are connected to ground and the target feature is electrically insulated;

wherein the current center position has the minimum gray level in the image of the test structure.

20. The apparatus as claimed in claim 17, wherein the target feature is connected to ground and the reference features are electrically insulated;

wherein the current center position has the maximum gray level in the image of the test structure.

* * * * *